United States Patent [19]
Christensen

[11] Patent Number: 5,336,160
[45] Date of Patent: Aug. 9, 1994

[54] MULTI-PURPOSE WILDERNESS SPLINT

[75] Inventor: Anna Christensen, Burnaby, Canada

[73] Assignee: Wilderness Alert Safety Products Ltd., Vancouver, Canada

[21] Appl. No.: 912,707

[22] Filed: Jul. 13, 1992

[51] Int. Cl.⁵ .............................................. A61F 5/04
[52] U.S. Cl. ................................... 602/6; 602/16; 602/18; 602/20; 602/27
[58] Field of Search ............... 602/5, 6, 16, 18, 20, 602/27

[56] References Cited

U.S. PATENT DOCUMENTS

| | | | |
|---|---|---|---|
| 3,496,934 | 2/1970 | Anderson | 602/16 |
| 4,520,806 | 6/1985 | Miller | 602/6 |
| 5,195,944 | 3/1993 | Schlogel | 602/6 X |

FOREIGN PATENT DOCUMENTS

| | | | |
|---|---|---|---|
| 1024082 | 6/1983 | U.S.S.R. | 602/5 |
| 11153 | 5/1916 | United Kingdom | 602/6 |
| 9014807 | 12/1990 | World Int. Prop. O. | 602/16 |

Primary Examiner—Steven A. Bratlie
Attorney, Agent, or Firm—Oyen Wiggs Green & Mutala

[57] ABSTRACT

A lightweight splint for use in wilderness or remote areas which is readily adaptable to multiple uses is disclosed. A single plastic strip is provided which can be adjustably positioned to form an arm splint having an adjustable angle, using a centrally located slit and an associated semi-circular array of apertures which can be secured in a variable orientation. The splint may also serve as a cervical or plantar splint.

8 Claims, 3 Drawing Sheets

MULTI-PURPOSE WILDERNESS SPLINT

TECHNICAL FIELD

The invention relates to the field of first aid devices for use in remote locations, and more particularly to a light weight, multi-purpose splint.

BACKGROUND ART

Those involved in wilderness activities such as back-country hiking and skiing, rock and mountain climbing and the like require first aid kits which are useful but light weight for carrying. A complete first aid kit should include a splint to immobilize a body member in the event of a fracture. Previously, a bendable but rigid piece of aluminum mesh has been carried to serve as a splint. Such material is expensive, and a splint made of such material is difficult to apply to the different splinting requirements,-such as a cervical splint to secure a fractured neck, or a plantar splint to secure a fractured ankle. It requires previous training of the user to use such splints to the various medical needs.

There is therefore a need for a lightweight splint for use in wilderness or remote areas which is readily adaptable to multiple uses.

DISCLOSURE OF INVENTION

A lightweight splint for use in wilderness or remote areas which is readily adaptable to multiple uses is disclosed. A single plastic strip is provided which can be adjustably positioned to form an arm splint having an adjustable angle, using a centrally located slit and an associated semi-circular array of apertures which can be secured in a variable orientation. The splint may also serve as a cervical or plantar splint.

BRIEF DESCRIPTION OF DRAWINGS

A preferred embodiment of the invention is disclosed in the accompanying drawings in which.

BEST MODE(S) FOR CARRYING OUT THE INVENTION

Figure 1:
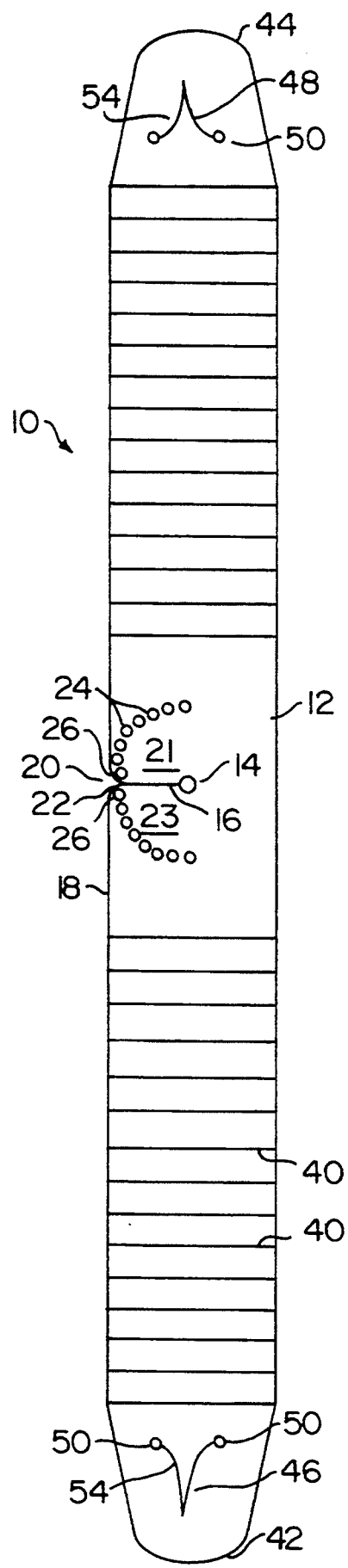
FIG. 1 is a plan view of the invention.

With reference to the drawings, the splint of the invention is designated generally as 10. It consists of a single elongated strip of a semi-rigid plastic 12, such as polyethylene or polypropylene, although other plastics would also be suitable, of a thickness of approximately 1 mm. The plastic strip 12 should be bendable and foldable for the various applications described as follows, while at the same time providing some rigidity and resistance to bending, particularly in the transverse direction. The overall length of the strip is approximately 48 inches or 120 cm. and the strip is about 5½ inches or 14 cm. wide in the central area.

At the mid-point of the strip 12, both in length and width, a small hole 14 of diameter approximately ¼-inch or 0.6 cm is formed. A slot 16 is cut at right angles to the outer edge 18 of the strip, from the edge in to hole 14. This forms two adjacent flaps 21, 23 with corners 20, 22 where the slot 16 meets edge 18 which are preferably rounded.

Figure 5:
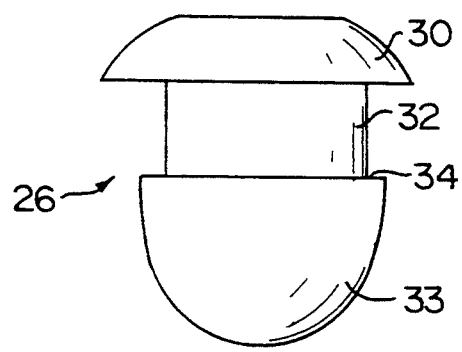
FIG. 5 is an elevation of the pin used in the invention.

A semi-circular array of holes 24 is also provided, centred on hole 14, each hole 24 also having a diameter of about ¼-inch or 0.6 cm. While 16 holes in total are illustrated, this number may be increased or decreased according to the amount of adjustability desired. Two pins 26, of the type illustrated in FIG. 5, are provided in two of the holes 24, pointing in opposite directions. The pins have circular head 30 which is greater in diameter than holes 24, and a shaft 32 which has a rounded end 33 having a maximum diameter less than head 30 but slightly greater than the diameter of holes 24, while the width of the shaft 32 between shoulder 34 and head 30 is less than the diameter of holes 24. In this way the shafts 32 of pins 26 can be forced through holes 24 and be held in place in the holes 24 until forcibly removed. The distance between the underside of head 30 and shoulder 34 is sufficient to accommodate two thicknesses of the plastic strip 12.

The plastic strip 12 is scored along a number of lines 40 which extend perpendicularly to the edges of strip 12. Preferably the scoring lines are spaced about 1 inch (2.5 cm.) apart, but this can again be varied depending on the amount of adjustability required. The scoring is sufficiently deep to permit the plastic to be accurately bent along the score line, while leaving sufficient strength in the plastic that it can be returned to its original shape for re-use. Ideally the material in this area would be a plastic of the "living hinge" variety which would allow complete recovery of the material in the folded area.

The ends 42, 44 of the strip 12 are rounded to avoid sharp corners. Each end is provided with holes 46, 48 approximately 1 inch to 2 inches (2.5 to 5 cm.) across to receive a rope or bandage. Holes 46, 48 can be formed by forming two holes 50 which connect with two curving slots 54.

Figure 2:
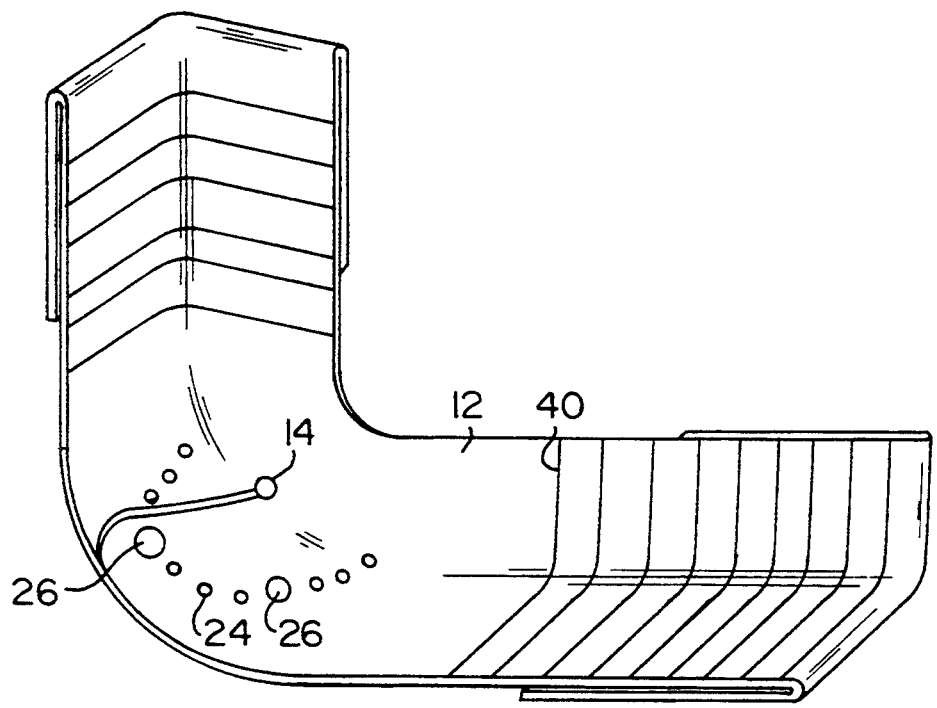
FIG. 2 is a perspective view of the invention in use as an arm splint.

As illustrated in FIG. 2, the invention is adapted for use as an arm splint as follows. Normally the pins 26 will be located in the two holes 24 which are closest to corners 20, 22, pointing in opposite directions in holes 24. The two halves of strip 12 are then rotated towards each other in roughly the same plane about hole 14, with one flap 21 overlapping the other flap 23. When the desired angle between the two halves (between 180 degrees and 90 degrees) is reached, the two ends of pins 26 are inserted through the respective overlying or underlying holes 24 to secure the splint in that position. The ends 42, 44 of the strip are then folded over along the desired score lines 40 to adjust the lengths of the respective ends of the splint. The patient's elbow can then be placed in the elbow area of the splint thus formed adjacent hole 14. The strip is then folded to conform to the patient's arm and bandages, tape or the like will then be wrapped around the splint containing the patient's arm at spaced locations to secure it rigidly against the splint.

Figure 3:
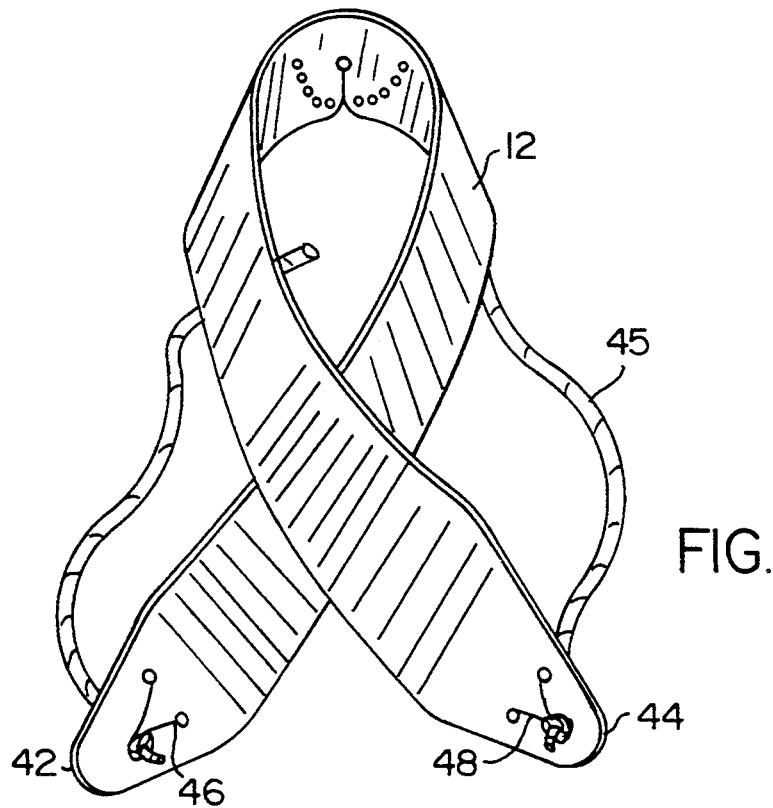
FIG. 3 is a perspective view of the invention in use as a cervical splint.

The invention may also serve as a cervical splint, as shown in FIG. 3. The centre of the strip 12 is placed around the patient's neck and the ends drawn down in overlapping relationship as shown in FIG. 3, in a scarf-like manner. A bandage, rope 45 or the like is knotted through the two holes 46, 48 and then tied around the back of the patient. This draws the splint tightly and rigidly around the neck of the patient.

Figure 4:
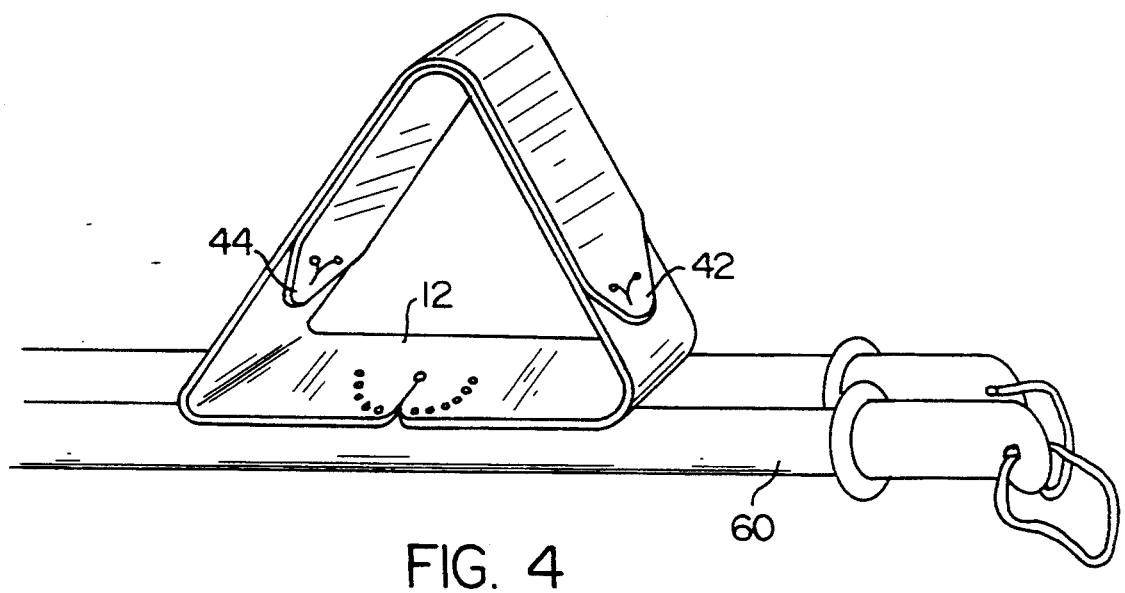
FIG. 4 is a perspective view of the invention in use as a plantar splint.

The invention may also serve as a plantar splint, as shown in FIG. 4. The centre of the strip 12 is placed on a flat surface, such as the ski poles 60 illustrated in FIG. 4 and may be secured to the ski poles by bandages or the like. 60 degree folds are then made along scoring lines 40 at spaced locations along either half of the strip to form an equilateral triangle as shown in FIG. 4. The patient's foot may then be placed within the triangle, heel down, and secured in the triangle by bandages or tape to secure the foot against rotation. The strip can also be folded flat and used as a flat splint in the usual way against a leg, arm or other body member, or wrapped around the member to provide rigidity if appropriate.

While the drawings show the edge of the strip as a flat edge, in order to make the device more comfortable for the user, a ¼-inch bead can be formed around the edge of strip 12 to cushion the edges against the user.

As will be apparent to those skilled in the art in the light of the foregoing disclosure, many alterations and modifications are possible in the practice of this invention without departing from the spirit or scope thereof. For example, while preferred dimensions for the invention have been provided, it will be apparent that other dimensions will be useful. For example, the strip could be between 3 and 8 inches in width and between 24 inches and 60 inches in length. Accordingly, the scope of the invention is to be construed in accordance with the substance defined by the following claims.

What is claimed is:

1. A multi-purpose splint comprising an elongated, foldable strip of semi-rigid material, having upper and lower surfaces, two lateral edges running along either side of said surfaces, and first and second ends, comprising
    a) a slit extending, in the area of said strip centrally located between said first and second ends thereof, from one of said lateral edges to a point midway between said lateral edges, said slit thereby forming first and second flaps, the second of said lateral edges being unbroken in the area of said strip opposite said midway point;
    b) a semi-circular array of apertures in said first and second flaps describing an arc around said midway point; and
    c) pin means extending through said apertures for securing one of said flaps in a position overlapping the other of said flaps;

whereby one of said ends may be rotated relative to the other of said ends about said midway point, thereby causing said apertures on one of said flaps to overlie said apertures on the other of said flaps, and said pin means may be removably extended through said overlying apertures to thereby form an angle between said first and second ends.

2. The splint of claim 1 further comprising a parallel array of scoring lines extending between said lateral edges on one of said surfaces to facilitate the folding of said strip at a desired length.

3. The splint of claim 1 wherein said first and second ends are provided with apertures for receiving a rope or bandage.

4. The splint of claim 3 wherein said area of said strip centrally located between said first and second ends of said strip is approximately 5 to 6 inches in width.

5. The splint of claim 1 wherein said midway point comprises an aperture.

6. The splint of claim 1 wherein said strip is between 3 and 8 inches in width and between 24 inches and 60 inches in length.

7. The splint of claim 1 wherein said strip is approximately 5 to 6 inches in width and between 44 inches and 52 inches in length.

8. The splint of claim 1 wherein said strip is formed of a plastic approximately 0.04 inches in thickness.

* * * * *